United States Patent [19]

Inoue et al.

[11] Patent Number: 4,876,204

[45] Date of Patent: Oct. 24, 1989

[54] METHOD AND APPARATUS OF AUTOMATIC CONTINUOUS ANALYSIS USING ANALYTICAL IMPLEMENT

[75] Inventors: Kazushige Inoue, Ibaraki; Hiroshi Yamamoto, Uji; Hiroshi Hyodo, Kyoto; Shinichi Kishimoto, Kuze, all of Japan

[73] Assignee: Kabushiki Kaisha Kyoto Daiichi Kagaku, Kyoto, Japan

[21] Appl. No.: 782,356

[22] Filed: Oct. 1, 1985

[30] Foreign Application Priority Data

Oct. 11, 1984 [JP] Japan .................................. 59-213592
Nov. 5, 1984 [JP] Japan .................................. 58-232678

[51] Int. Cl.⁴ ............................................ G01N 35/04
[52] U.S. Cl. ........................................ 436/46; 422/63; 422/64; 422/65; 436/47; 436/48
[58] Field of Search ............... 422/63, 64, 65; 436/47, 436/48; 414/222, 225, 223; 901/17; 221/171, 173, 236

[56] References Cited

U.S. PATENT DOCUMENTS

| | | | |
|---|---|---|---|
| 2,652,139 | 9/1953 | Baehr et al. ........................... | 221/173 |
| 3,645,690 | 2/1972 | Rochte et al. ......................... | 436/48 |
| 3,760,956 | 9/1973 | Burch ..................................... | 901/17 |
| 3,918,910 | 11/1975 | Soza et al. .............................. | 422/66 |
| 3,951,271 | 4/1976 | Mette ..................................... | 901/17 |
| 4,152,390 | 5/1979 | Noseo et al. ........................... | 422/63 |
| 4,204,610 | 5/1980 | Schlaepfer ............................. | 221/171 |
| 4,451,433 | 5/1984 | Yamashita et al. .................... | 422/100 |

*Primary Examiner*—Michael S. Marcus
*Attorney, Agent, or Firm*—Darby & Darby

[57] ABSTRACT

An autonomous continuous analysis method and apparatus using Dip and Read type analytical implements. A series of operations of taking out analytical implements, dipping them in the sample solution, optical measurement, calculation, and disposal of the used sample solution are performed automatically.

The dip stage, in particular, is automated by use of an analytical-implement automatic supply device and an analytical implement automatic handling device which, holding an analytical implement, dips it in the sample solution, and sets it on a reaction turntable. A number of analytical implements are put in a storage section comprising a bottom section provided with an analytical implement groove and at least one inside surface which is parallel with the groove, are taken out one by one by the relative movement of the groove and in normal and reverse direction and by stopping in a specified position after confirming by a detector that an implement has been caught in the groove.

13 Claims, 11 Drawing Sheets

METHOD AND APPARATUS OF AUTOMATIC CONTINUOUS ANALYSIS USING ANALYTICAL IMPLEMENT

BACKGROUND OF THE INVENTION

This invention relates to a method and an apparatus of automatic continuous analysis using an analytical implement which effects taking out the implement, dipping it into a sample solution, performing optical measurement, calculation and disposal of the used sample solution, all automatically.

The analytical implement (2) most widely used today in the analysis of blood, urine and the like has a structure such as that shown in FIG. 3, comprising a transparent plastic strip (2A) provided at one end, a number of reagent sections (2B) corresponding to the number of measuring items and a holding section (2C) at the other end. The reagent sections shown in FIG. 3 are small pieces of filter paper impregnated with a reagent which are bonded to the strip with double-faced adhesive tape (2D). Another form of reagent section (2B) is also available which is a reagent coated together with a base material on the strip to form a film.

There are also other types of analytical implements which are provided near the reagent section (2B) with a reference reflector or on the holding section (2C) with a coating layer (2E) for distinguishing the type and fitting face or position of the reagent section (2B). Those types using black adhesive tape are often used to facilitate optical measurement.

These analytical implements were originally used in the "Dip-and-Read" inspection which determines the concentration of a material by comparison of the color of the implement after being dipped in the solution to be examined with the reference color.

At present, the "read" stage is carried out by instrument to effect determination and, in some cases, the processes of optical measurement, calculation, display of concentration, and the discharge of the analytical implement have been automated.

In contrast, the "dip" stage is still done by manual operation. Each analytical implement is taken out, one at a time, from a closed vessel, set to the optical instrument after being dipped in the sample solution, and disposed of after the measurement has been completed, all manually. This can be a big burden on the operator, particularly when the number of specimens is large. In addition, a certain reaction time is inherent which occupies the operator completely during the measuring. In manual operation, furthermore, variations of the dipping time and the time after dipping until the start of measurement becomes inevitable, resulting in measurement errors. Therefore, it is desirable with regard to cost, accuracy and other points, particularly when treating a large number of specimens, to make the measuring completely automatic, including the "dip" stage.

The complete automation including the "dip" stage, however, requires a device that regularly takes out the analytical implement from the vessel or storage, and also requires an analytical implement automatic handling device which dips the analytical implement, which has been taken out of the vessel or storage, in the sample solution and sets it accurately into the optical measurement section. These devices are required to work accurately and are preferably small-sized and inexpensive. Analytical implements mentioned above are stored in a closed vessel containing a desiccant with their holding sections (2C) directed outward and reagent sections (2B) being directed at random. Thus, it is difficult to take them out automatically.

SUMMARY OF THE INVENTION

It is an object of the invention to provide a method for attaining automatically and continuously all the processes of Dip-and-Read using an analytical implement having a holding section and reagent sections as shown in FIG. 3; that is, forwarding the analytical implements one by one, dipping and transferring the implements, measuring, including optical measuring and calculation, and after-treatment processing, including disposal.

Another object of the invention is to provide an automatic continuous measuring method using analytical implements on the market which are available by visual determination.

Still another object of the invention is to provide a method for accurate measurement with decreased variation of dipping time and of the time after the dipping to the start of measurement and with a substantial reduced burden on the operator.

A further object of the invention is to provide a method of forwarding accurately, one-by-one, the analytical implements out of the storage of many pieces (stored dry as required), so that each can be gripped by the analytical implement holder of the operation device.

Still a further object of the invention is to provide an analysis apparatus which automatically and continuously treats the total stages of Dip-and-Read by coordinating an analytical implement automatic supply device, analytical implement automtic supply device, and a known optical measurement device.

Another object of the invention is to provide a novel and positive automatic supply device of analytical implements.

BRIEF DESCRIPTION OF THE DRAWINGS

FIG. 3 is a side view of an example of the analytical implement used in the invention.

FIGS. 4 to 8 show an embodiment of the analytical implement automatic supply device according to the invention, wherein FIG. 4 is a perspective view of the whole apparatus, FIG. 5 is a vertical section showing the moving range of the bottom, FIG. 6 is a block diagram of the same, FIG. 7 is a partially sectional view of the same, and FIG 8($a$), ($b$) and ($c$) are an illustration of inverting the analytical implement.

DETAILED DESCRIPTION OF THE INVENTION

With reference to the drawings, the invention is now described in detail based on the embodiments.

A. Outline of the Whole Apparatus

Figure 1:
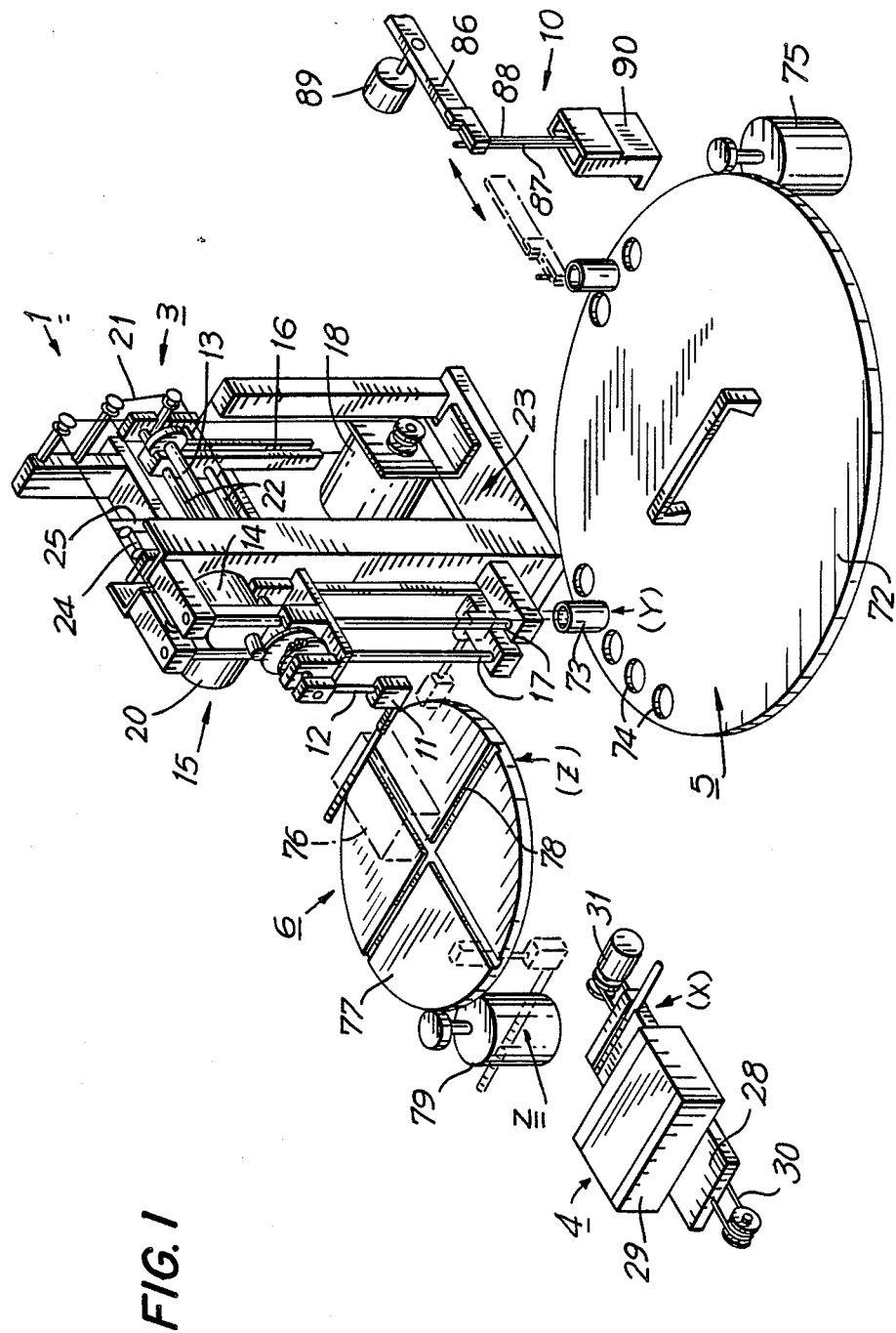
FIG. 1 is a schematic perspective view showing an embodiment of the apparatus according to the invention.
Figure 2:
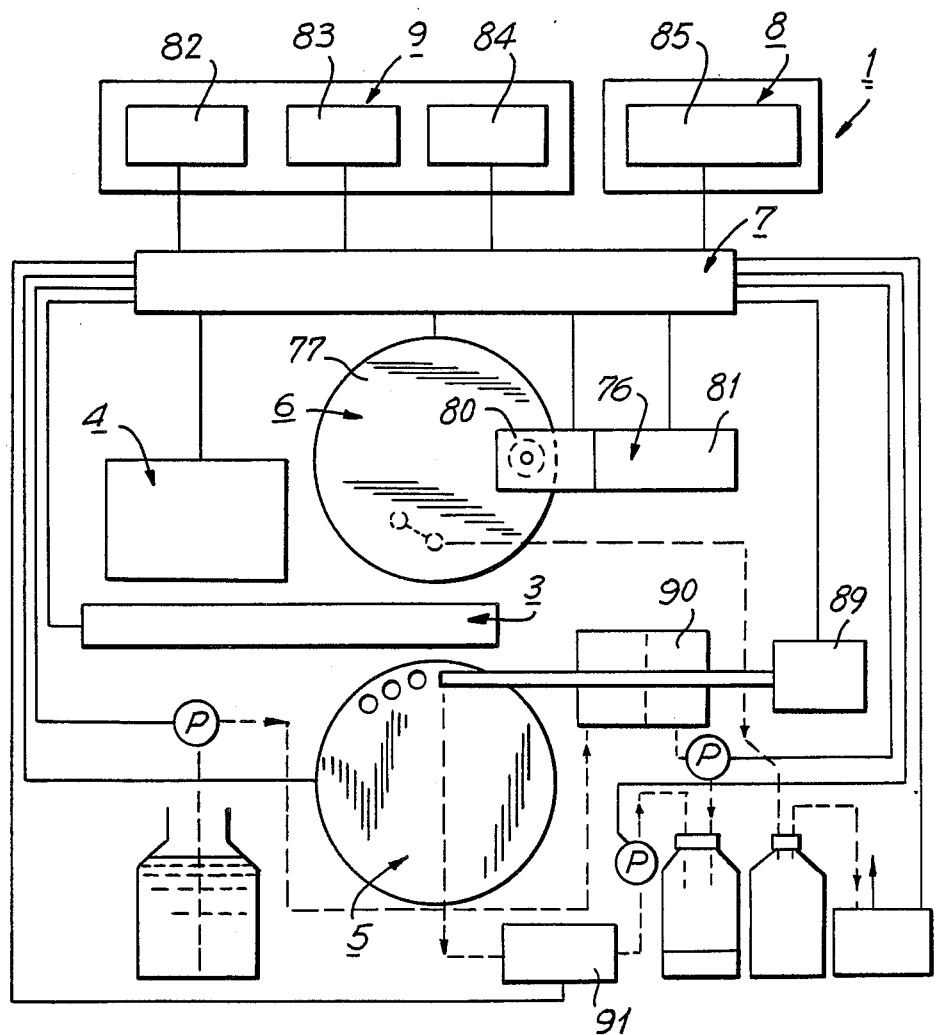
FIG. 2 is a block diagram of the same apparatus.

FIG. 1 is a schematic perspective view showing the working conditions of an embodiment of the apparatus according to the invention; and FIG. 2 is its block diagram. The automatic continuous analysis apparatus 1 using this analytical implement comprises an analytical implement automatic supply device 4, a sample-vessel supply device 5 and an optical measurement device around an analytical implement handling device. The relative positions of the devices shown in FIG. 1 is explained in relation of the analytical implement automatic handling device 3. The analytical implement automatic supply device 3 is arranged so that the held part of the implement is located beneath the extension of the shaft 13 which is equipped with the holder for the analytical implement being ready for analysis. When the arm 12 rotates 90° counterclockwise around the axis of the shaft 13, none of the ports 74 being formed on the turntable 72 in the sample-vessel supply device takes the position right under the holder 11. Then, the position is the place where the analytical implement is dipped into the sample vessel. It is necessary to put back the arm 12 by right-and-left driving shafts 22 after holding the analytical implement in the holder 11 at the analytical implement automatic supply device 4 to bring the analytical implement to the position where the analytical implement is dipped into the sample vessel. When the arm 12 rotates 90° clockwise around the axis of the shaft 13, one of the grooves 78 which are formed on the turntable 77 in the optical measurement device 6 to accept the analytical implement should take the position directly under the analytical implement. (It is possible to adjust the relative position of the groove and the analytical implement in right-and-left direction). In FIG. 2, reference numeral 7 indicates a control section provided with a CPU, clock device, etc., numeral 8 indicates an input section, and 9, an output section.

B. Analytical implement Automatic Handling Device

The analytical implement automatic handling device 3 comprises an arm 12 provided with an analytical implement holder 11 on its end and an arm driving means. The arm driving means comprise a rotating section 15, a vertically driving section, and a right-and-left driving section. The rotating section comprises an arm 12, an arm driving shaft 13, and a shaft rotating motor 14. The vertically driving section comprises a vertically driving motor 18, a wire 19, and shafts 17. The right-and-left driving section comprises a right-and-left driving motor 20 and shafts 22.

The rotating section 15 is supported by vertical shafts 17, and hung movably in up-and-down direction with the wire 19 wound endlessly around the shaft of the vertically driving motor 18. A slider 16, which supports one end of the arm driving shaft 13 to prevent inclining, is supported movably in right-and left direction by shafts 22. The slider 16 is driven in right-and-left direction with a wire 21 wound endlessly around the shaft of the right-and-left driving motor 20.

Therefore, when the vertically driving motor 18 rotates, the wire 19 revolves as a whole along the pulley. Furthermore, the rotating section 15 that is hung from the wire 19 moves in an up-and-down direction. At this time, the shaft 13 and motors 14 and 20 move similarly in an up-and-down direction, but shaft 22 doesn't move. Next, when the right-and-left driving motor 20 rotates, the wire 21 revolves as a whole along the pulley. Furthermore, the slider 16 and the shaft 13 move in a right-and-left direction; therefore the arm 12 moves in a right-and-left direction.

Then, when the shaft rotating motor 14 rotates, a disc that is connected with the shaft of the motor revolves; therefore the shaft 13 revolves and eventually the arm 12 turns.

As mentioned above, the arm 12 is driven in three directions by individual drives.

The analytical implement holder 11 of this embodiment has a grip device which is opened and closed by pushing and pulling of a release 24. (The release 24 utilizes a wire passing through the inside of a guide pipe, and can be operated by pushing and pulling of the wire. It has similar structure to a release which remotely controls the shutter of a camera.) The release 24 is operated by a solenoid 25 in this embodiment. The grip device is shown in FIG. 16. The guide pipe of the release 24 is connected with the upper part of the analytical implement holder 11, and the internal wire is connected with the lower pinching materials of the grip device. Therefore, the grip device is opened and closed by pushing and pulling of the wire in the release, by which the analytical implement can be gripped and released.

The operation of the release 24 may also be affected by an air cylinder or rotating cam, and besides the operation of the grip device, may be directly effected by a solenoid or air cylinder.

A system which directly holds the analytical implement by air suction instead of the grip device may be used.

The release type is generally preferable since it is light and strong. These releases and air pipe may be passed through the arm 12, or may be directly connected with the analytical implement holder 11 apart from the arm.

Motors 14, 18 and 20 are preferably pulse motors suitable for accurate positioning.

The analytical implement automatic handling device 3 is not limited to the one shown in the drawings. A small-sized simple robot or any structure than can move the arm 12 up-and-down, right-and-left, and in circular motion by use of a motor and wire, screw thread, cylinder, etc., can be used.

C. Analytical Implement Automatic Supply Device

The analytical implement automatic supply device 4 is for supplying analytical implements one by one, and various structures are encompassed.

Figures 3, 4:
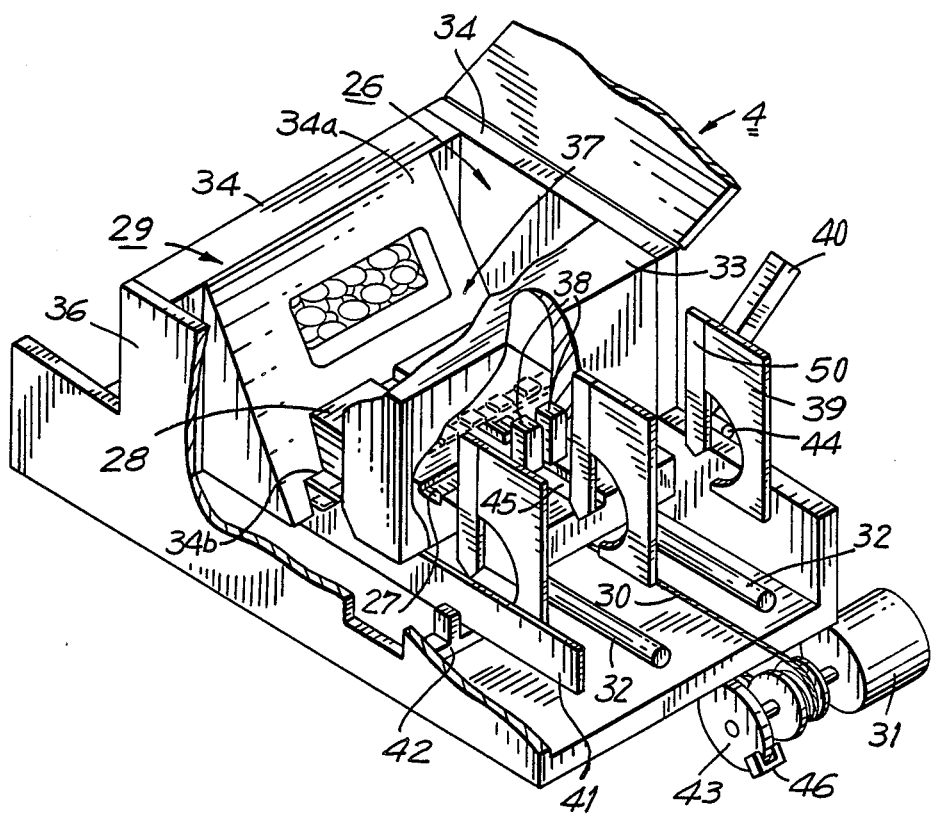

In this embodiment, a hopper type as shown in FIG. 4 to FIG. 14 is used. The hopper 26 for putting in analytical implements comprises a bottom section 28 provided with an analytical implement groove 27 and a side section 29 comprising four walls. The space formed by hopper 26 is the storage section 37. The hopper moves the analytical implement groove 27 to the outside of the hopper by sliding the bottom section 28. The movement of the bottom section 28 is driven by a motor 31 through a wire 30 connected with the front and back of the bottom section 28. The wire 30 is an endless wire and is supported by a pulley positioned in opposition to the motor 31 on the bottom section 28. In FIG. 4, the pulley is behind a wall section 34. The motor 31 is preferably pulse motor.

Figure 5:
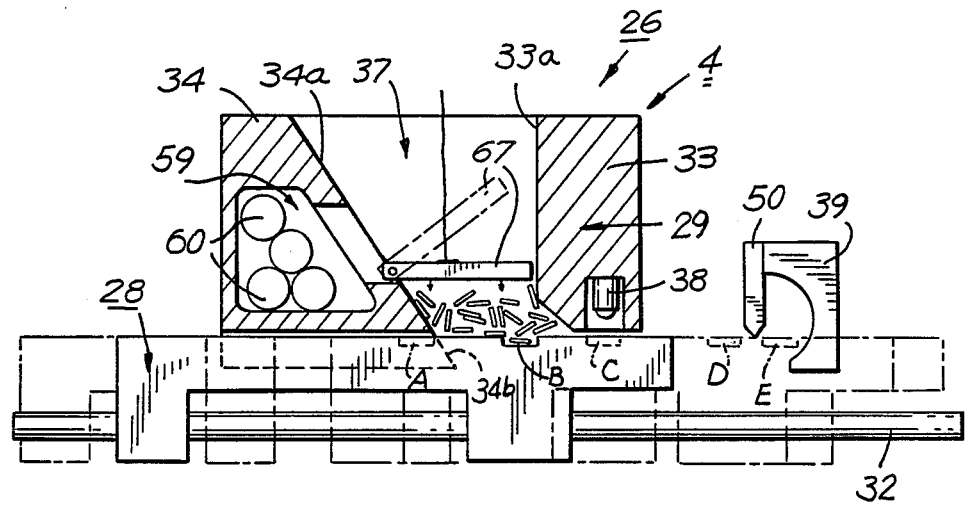
Figure 6:
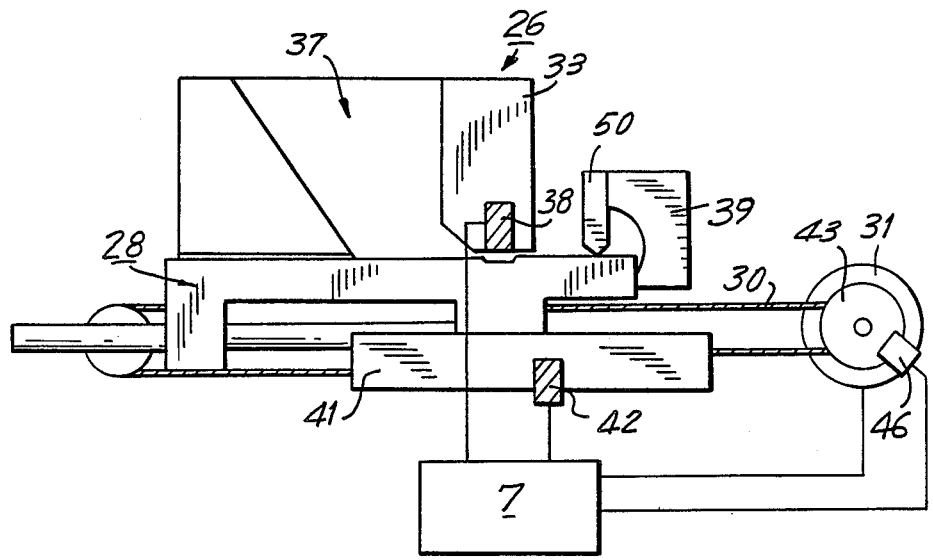
Figure 7:
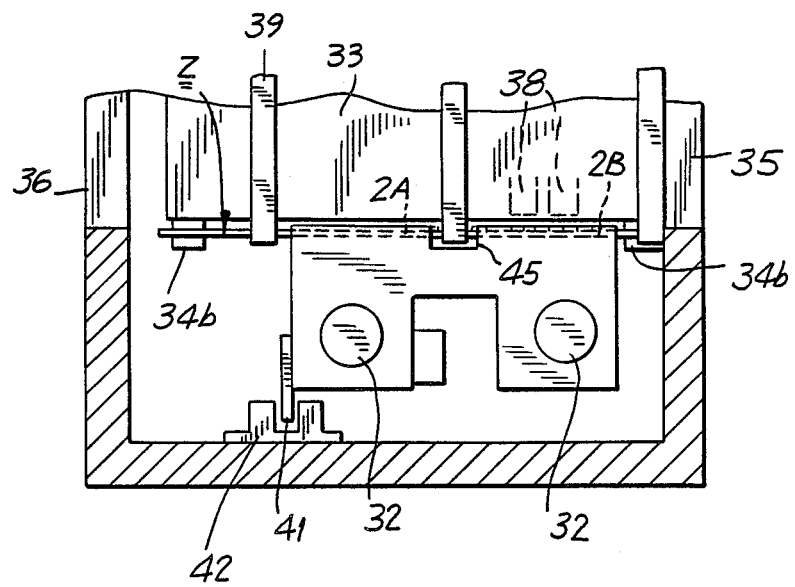

The structure and behavior of the analytical implement automatic supply device are now described in detail. FIG. 4 is a perspective view showing an example of the analytical implement automatic supply device 4, FIGS. 5 and 6 are its vertical sections, and FIG. 7 is in partial section.

On the top face of the bottom section 28, the analytical implement groove 27 is provided at right angles to the moving direction of the bottom section 28, for accommodating only one piece of the analytical implement 2. The side section 29 comprises two wall sections 33 and 34 intersecting at right angles to the moving direction of the bottom section and two wall sections 35 and 36 which are parallel with the moving direction of the bottom section 28. The inside surfaces 33a and 34a of the wall sections 33 and 34 are parallel with the groove 27 viewed in plan (the lower edges of the inside surfaces of walls are parallel with the longitudinal direction of the groove 27) and the section enclosed by the four inside surfaces of walls and the bottom forms a storage section 37 for analytical implements 2. The bottom section 28 is narrower than the space between the wall sections 35 and 36 and is provided with some clearances therebetween.

In these drawings, reference number 38 indicates a detector for detecting the presence of analytical implements 2, 39 is the inverting plate of an inverting device, 40 is a presser lever for pressing the analytical implement 2 in the groove 27 which has stopped outside the hopper, 41 is a shade fixed to the lower side face of the bottom section, 42 is a detector provided on the side of the shade 41 for detecting the position of the bottom section 28, and 43 is a rotary encoder attached to the shaft of the motor 31.

The operation of the analytical implement automatic supply device 4 is then described in the following paragraphs (i) to (x):

(i) The bottom section 28 is supported by two slide shafts 32, 32 inserted therethrough, and moved by the motor 31 in normal and reverse directions (right and left in FIGS. 5 and 6) through movement of the wire 30. The moving range is from position A (where the analytical implement groove 27 somewhat exceeds the left inside wall surface (34a)) to position D (where the outside of the right wall section 33 stops) in FIG. 5. In this range, it passes position B (in storage section 37) and position C (where it exceeds the right inside wall surface (33a) (position of the detector 38). Further, it moves, as required, to the inversion position E exceeding the stopping position D. (Inversion is described later.)

In this embodiment, the movement of the bottom section 28 is reversed when the groove 27 comes to position A and to position D by the reversal of the motor 31 according to the signal given by the detector 24 detecting the shade 41 which is not present. Upon receiving a signal that the analytical implement is reverse in bottom-top direction, the motor rotates further for certain pulses or time to send the bottom section 28 in the normal direction.

(ii) The bottom section 28 goes back to position A after the analytical implement has been taken out of the groove 27 which is stopped at position D. Then, the bottom section goes forward. After taking a new analytical implement into the groove 27 and being checked by the detector 38 at position C for the possession of an analytical implement, it goes further forward until the groove 27 comes to position D.

With the bottom section 28 stopped in position, the presser lever 40, which is driven by the motor 44, presses down the analytical implement 2 into the groove 27. This is to secure the holding of the analytical implement 2 by the analytical implement holder 11, thus, suppressing floating.

(iii) The suspension continues until the next action command is delivered. The action command is delivered by the control section 7 after a specified time has elapsed from the end of the preceding suspension or after detecting the fact that the analytical implement automatic handling device has taken out the analytical implement 2 from the groove 27. If no analytical implement is found in the groove 27, the bottom section 28 goes back from position C and continues the reciprocating motion until an analytical implement 2 is caught by the groove 27.

(iv) Since the inside wall surfaces 33a, 34a (or at least their bases) are parallel with the groove 27, the analytical implements 2 are arranged in parallel with the groove 27 in the inside wall section as the bottom section 28 moves and is then easily caught by the groove 27.

The left inside wall surface 34a, inclined as shown, is convenient for stirring the analytical implements in the inside wall section 34a and for taking an analytical implement 2 incompletely caught by the groove 27. To readily attain these objects, it is advisable to project both sides of the lower wall section 34b downward somewhat from the bottom surface. Further, it is preferable to provide a longitudinal groove 45 in nearly the center of the bottom section 28 and to project the center of the lower wall section 34b so that it fits in the longitudinal groove 45.

The inside wall surface 33a, in its right side, may be vertical, but is preferably chamfered to lead analytical implements, even with some warp, smoothly into the groove.

(v) On the other hand, it is necessary to stop the movement of the bottom sections 28 immediately when any disorder is detected, since if an analytical implement 2 is caught in the gap between the bottom section 28 and the bottom edge of the wall section 33, the reagent section 2B can be damaged.

A rotary encoder 43 is used as the disorder detecting mechanism in this embodiment. A detector 46, such as a transmission type photointerrupter, inputs regular light-and-dark pulse signals into the control section 7 as the bottom section 28 moves.

Upon production of a disorder, the pulse signals are disturbed. This is detected and the motor 31 is immediately stopped. An alternate system may be used in which the analytical implement 2 is moved in the reverse direction somewhat, and then in the normal direction. If no disorder is found, then the operation is continued as it it. To stop the rotation immediately when plugging occurs, the motor preferably has a weak torque or is provided with a clutch device which cuts the torque exceeding a specified value.

Figure 9:
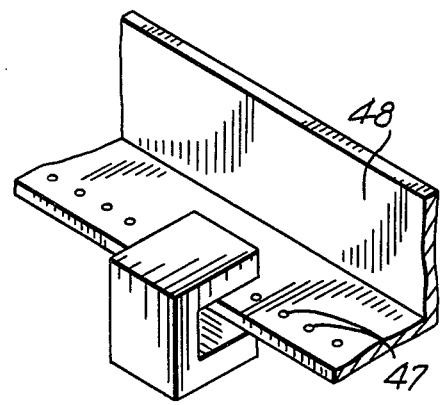
FIG. 9 is a schematic perspective view showing another embodiement of the disorder detecting device.

Another example of the detecting means is shown in FIG. 9. It has a perforated plate 48 having a number of small holes bored regularly in small intervals and fixed to the lower part of the bottom section 28. It is monitored by the detector 46 in the same manner as the above.

(vi) To check the presence of an analytical implement 2 in the groove 27, use of one detector 38 is sufficient. If a plurality of detectors, the same type or different types, are used, top-bottom judgement or detection or an unacceptable one becomes possible.

The presence of an analytical implement is detected, for example, by checking the shade of the analytical implement 2 (reagent section 2B or coating layer 2E) with a transmission type photo-interrupter. The top-bottom judgement is made, for example, from the difference of the quantity of reflected light from the top (reagent section 2B) and from the bottom (black adhesive tape 2D), using a reflection type photo-interrupter.

The detection of the presence and top-bottom judgment of an analytical implement may also be made as follows:

Stepwise threshold values are set by use of a reflection type photo-interrupter for quantities of reflected light from the groove 27 of the bottom section 28, from the strip 2A and adhesive tape 2D, and from the reagent section 2B, and they are discriminated by the control section 7, to effect detection of the presence and top-bottom judgement with the same detector. Also, similar means can be applied to the coating surface of the analytical implement 2, to effect the detection of the difference of the light reflected by the coating surface 2E, and detection of the presence and top-bottom judgment of an analytical implement from the quantity of light simultaneously.

Further, it is possible to provide a plurality of detectors 38 to monitor the individual reagent sections, to make discrimination of the type and inspection of defectives (e.g. those having peeled reagent section 2B or scar) by the variation of the quantity of reflected light, and to remove a non-conforming one (such as different types and defectives) out of the system. Various types of detectors 38 can be used in combination. The detectors 38 can be installed in various positions such as inside or outside of the wall section 33, not limited to those as shown.

(vii) Top-bottom judgment is required for arranging the reagent sections 2B to a certain direction when the analytical implement automatic handling device 3 mounts the analytical implement 2 on the reaction turntable of the optical measurement device after dipping them in the solution to be examined.

If the arm of the analytical implement automatic handling device 3 has the function to invert the analytical implement 2, it is sufficient to give to the analytical implement handling device 3 only the information that the top and bottom of the implement is inverted. Otherwise, those facing the wrong side must be inverted so that all the reagent sections 2B point in the same direction, upward or downward.

(viii) This inversion is effected by inversion plates 39 attached to a bar 49 mounted across the walls 35 and 36 above the inverting position E (FIG. 5). In this embodiment, the inversion plates 39 are positioned on both sides of the bottom section 28 and at the longitudinal groove 45.

Figure 8:
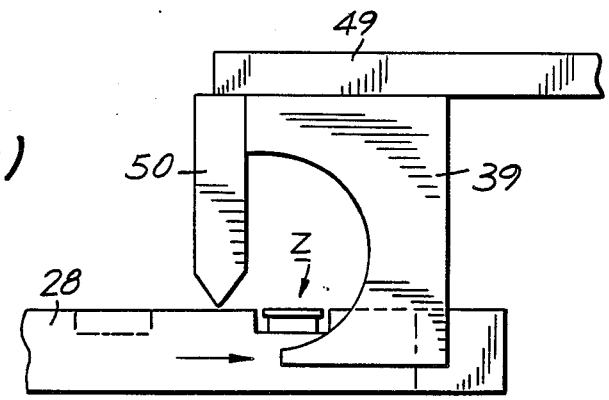
Figure 8:
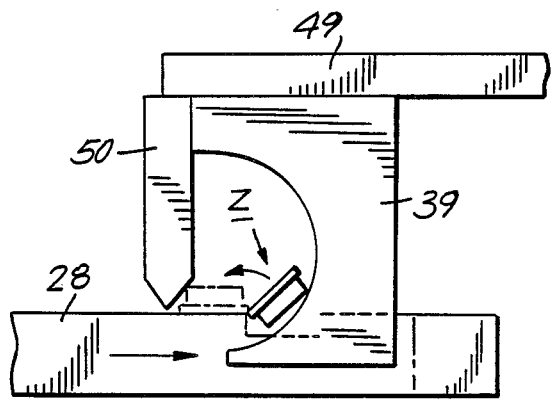
Figure 8:
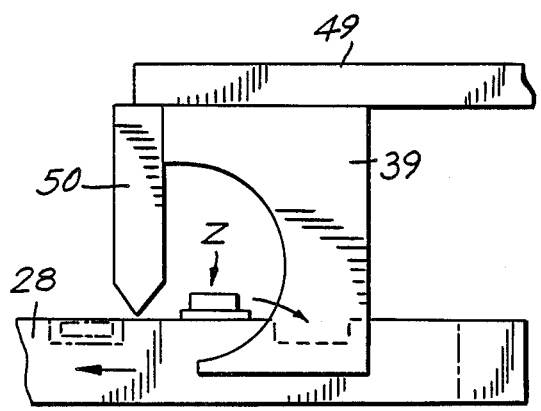

The action of the inversion mechanism is now described with reference to FIG. 8. Upon receiving a signal from the detector 38 indicating that the bottom-top direction of the analytical implement is wrong (FIG. 8(a)), the motor 31 makes excessive normal rotations for certain pulses or a certain time to bring the bottom section 28 to a position where the groove 27 goes over the rest position D (chain line in FIG. 8(a)). This inverts the analytical implement 2 in the groove 27 along the curved surfaces of the inversion plates 39 (FIG. 8(b)). Here, the analytical implement 2 is shifted toward the wall section 33 out of the groove 27.

Then, the bottom section 28 goes back and drops the analytical implement 2 into the groove 27 with the interceptors 50 which are united with the inversion plates 39 (FIG. 8(c)). It may be dropped by the bottom edge of the outer wall of the wall section 33, instead of the interceptor. The bottom section 28 successively goes back and is checked by the detector 38. If the reagent section 2B is ascertained to point upward correctly, the bottom section goes back from this point to the rest position D (chain line in FIG. 8(c)) of the groove.

Figure 10:
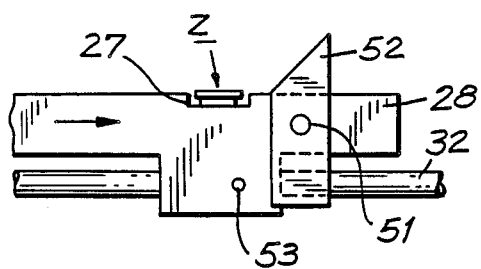
FIG. 10 ($a$), ($b$) and ($c$) are an illustration of inverting the analytical implement by another embodiment of the inverting device.
Figure 10:
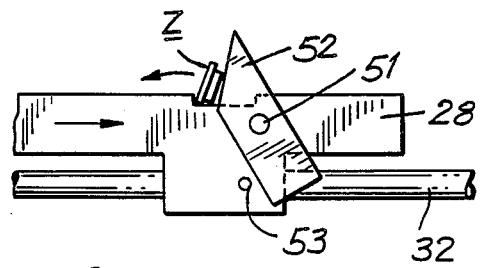
Figure 10C:
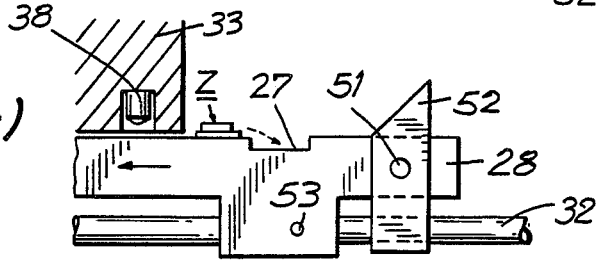

Another possible example of the inversion device is show in FIG. 10. It comprises levers 52 rotatably supported through a shaft by the wall sections 35 and 26 outside the hopper 26, and pins 53, 53 projecting toward both sides from the lower front of the bottom section 28. Upon receiving a signal from the detector 38 indicating that the bottom-top direction of the analytical implement is wrong (FIG. 10(a)), the bottom section 28 goes in normal direction and the levers 52 stand up, being pushed by pins 53 at their portions. This pushes out analytical implement 2 in the groove 27 and inverts it (FIG. 10(b)). The implement 2 which has been pushed out and inverted is then dropped back into the groove 27 by the bottom edge of the outer wall of the wall section 33.

Figure 12:
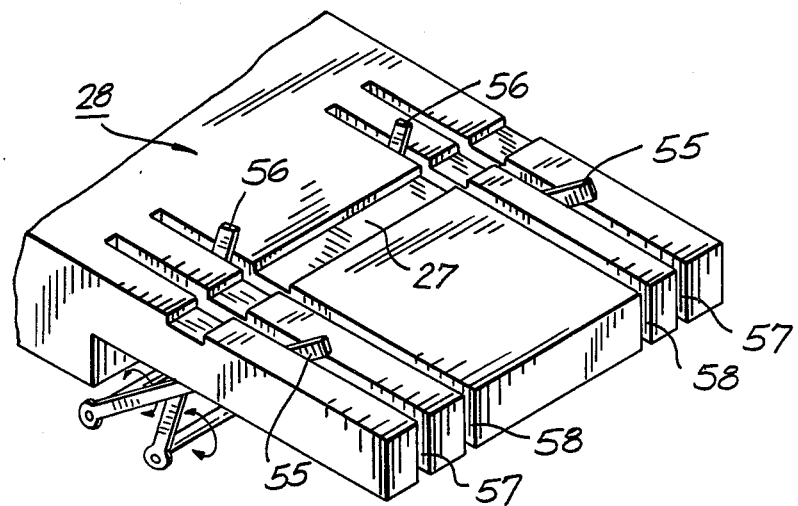
FIG. 12 is a perspective view showing still another embodiment of the inverting and removing device.

It is also possible, as shown in FIG. 12, to provide near the rest position D of the groove 27 levers 55, 55 which are driven by a motor, solenoid, etc., to invert the analytical implement.

(ix) Disposal of non-conforming analytical implements 1 is now described. Through analytical implements 2 are shipped after strict inspection, defectives such as those with peeled reagent section 2B may possibly be produced due to agitation in the hopper 26 and for other reasons. Moreover, when using different types of analytical implements 2 properly, there is a risk that another type may be mingled into a particular type. In such a case, usually abnormal measurements are obtained and remeasurement is performed. Remeasurement, however, takes much time and labor, and it is possible depending upon the degree of abnormality, that it is not noticed at all.

One possible method to deal with this problem is to deliver an instruction from the control section 7, when the detector 38 has detected a disorder, to once return the groove 27 to position B and take out a new analytical implement 2. Alternately, a mechanism to remove a non-conforming analytical implement may be provided.

Figure 11A:
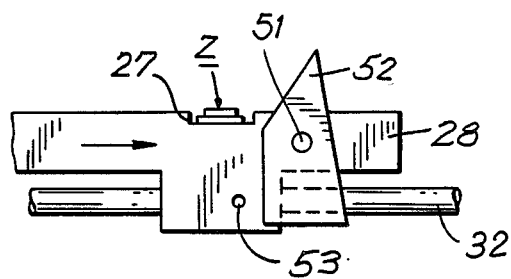
FIG. 11 ($a$), ($b$), ($c$) and ($d$) are an illustration of removing the analytical implement by use of the device shown in FIG. 10.
Figure 11B:
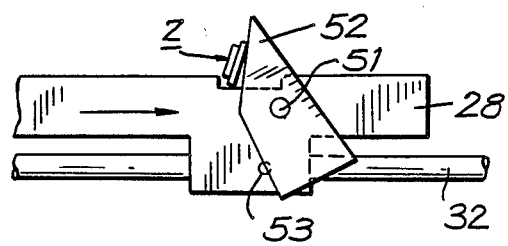
Figure 11C:
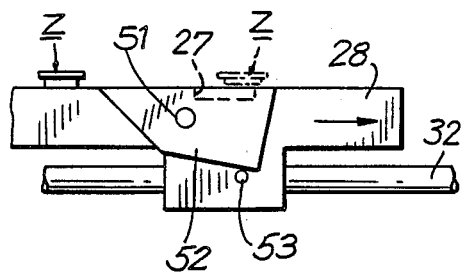
Figure 11D:
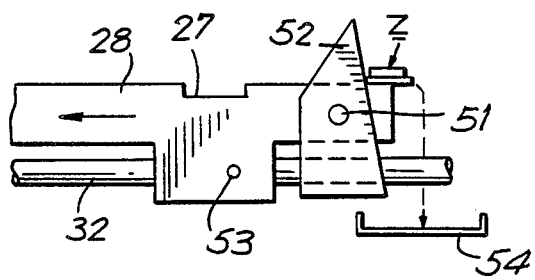

Various types of such mechanisms for removing non-conforming analytical implements are possible. The inversion device shown in FIG. 10, for example, can be used directly. An analytical implement 2, caught in the groove 27 in the normal direction as shown in FIG. 11(a), is inverted by the inversion levers 52 as shown in FIG. 1(b). The bottom section 28 is moved further in the normal direction to bring down the levers 52 (FIG. 11(c)). Then the bottom section 28 is moved backward to return the levers 52 to the original posture and moved further backward to release the analytical implement into chute 54 (FIG. 1(d)).

Levers 56, different from the levers 55 shown in FIG. 12, can be used for removing non-conforming implements and the levers 56 and 56 may be driven by motors independently from each other. In FIG. 12, the bottom section 28 is provided with longitudinal cuts 57 and 58 for passing levers 55 and 56 therethrough.

Figure 13:
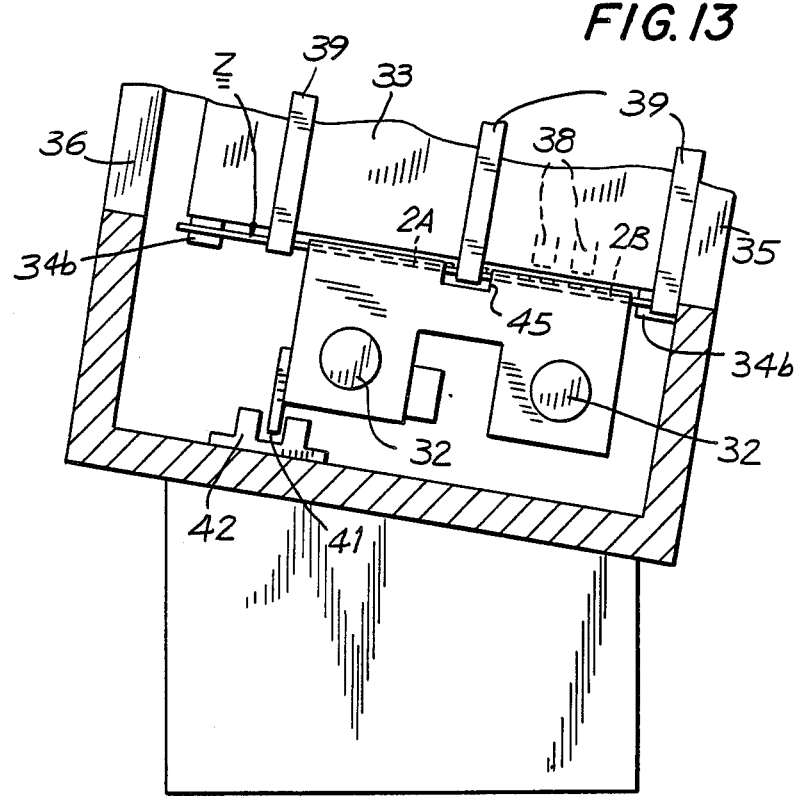
FIG. 13 is a sectional view of a modification of the analytical implement automatic supply device according to the invention.

(X) Modifications (1) The hopper 26 is tilted, for example, about 15° as shown in FIG. 13. This makes the ends of the analytical implement 2 even. Thereby, the grip position of the holding section 2C is made constant when the analytical implement is taken out by the automatic handling device 3, leading to accurate dipping.

(2) To keep the air in the storage section 37 dry, a desiccant storage 59 is provided inside or outside the hopper 26 connected to the storage section 37. An example of this type is shown in FIG. 4 and FIG. 5. The thick wall section accommodates a desiccant storage 59 which contains desiccant pieces 60. The hopper is preferably provided with a cover 61 to keep it dry.

Figure 14:
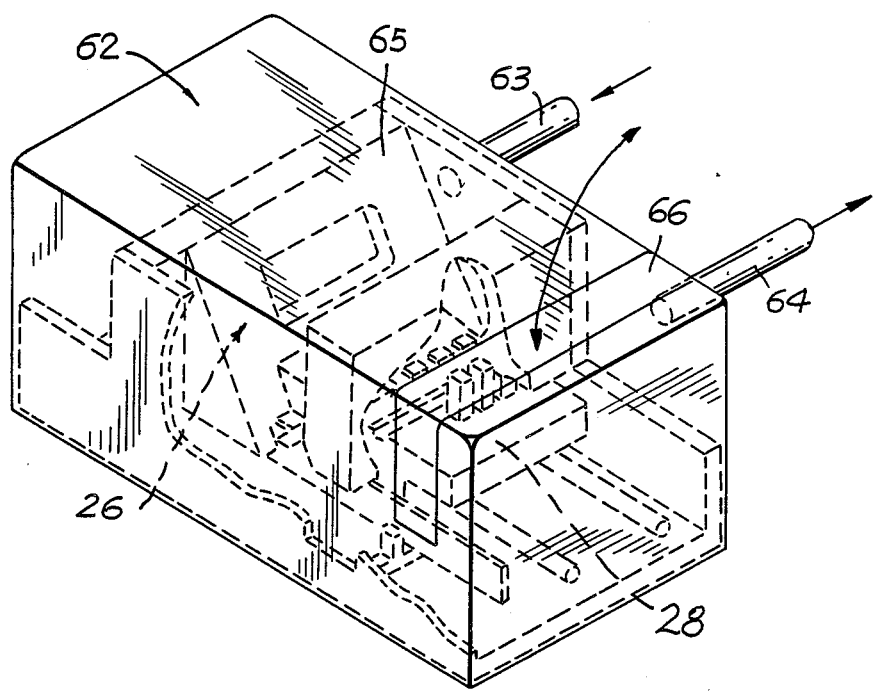
FIG. 14 is a perspective view of the device shown in FIG. 13.

(3) As shown in FIG. 14, the hopper 26 and the moving range of the bottom section 28 is enclosed by a cover 62 and dry air may be sent into this cover 62. The cover 62 is provided with pipes 63, 64 for circulating air, lid section 65, and opening cover 66 which automatically opens and closes when the analytical implement 2 is taken out.

(4) The analytical implement groove is provided with a suction port, through which air is sucked by an air pump. This brings a warped analytical implement in close contact with the groove 27 or presses a floating analytical implement (not shown).

(5) To check the residue of analytical implements 2 in the storage section 37, means such as optical sensor and counter for counting analytical implements which have been taken out is provided (not shown).

(6) As shown in FIG. 4 and FIG. 5, a weight 67 is provided in the storage section 37. This suppresses a large increase of analytical implements in the storage section 37 and helps them to snugly fit in the groove 27. The end of the weight 67 is connected to the lid with wire 68 so that the weight 67 is lifted when the lid 61 is opened.

(7) According to the invention, the bottom section 28 and the side section 29 may be moved relatively. Each wall section 33, 34, 35, 36 may be moved with the bottom section 28 fixed, or only the wall sections 33 and 34 may be moved.

D. Other Analytical Implement Automatic Supply Devices

In addition to the above-described analytical implement supply device, a cassette type can be used.

Figure 15:
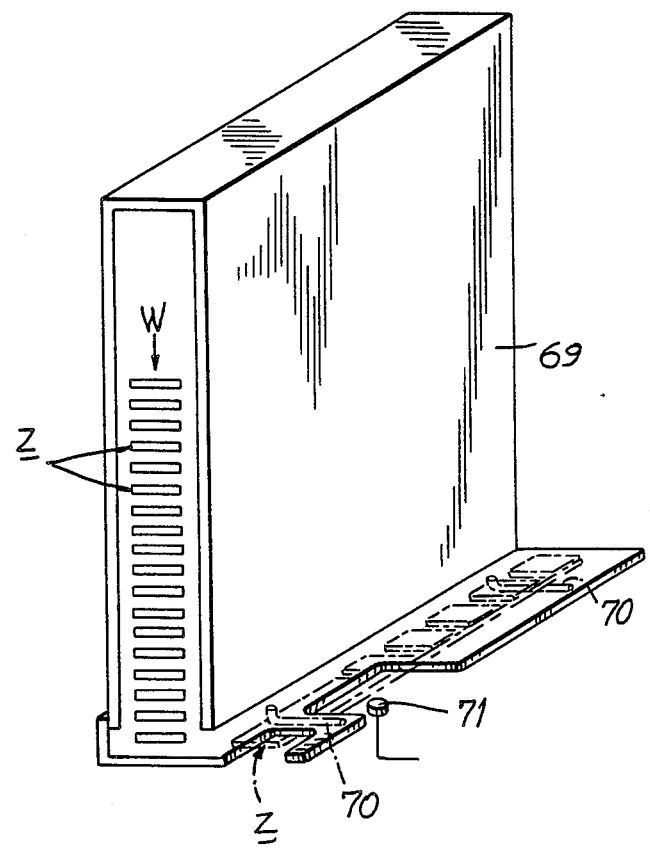
FIG. 15 is a perspective view showing an embodiment of the analytical implement cassette-type automatic supply device.

FIG. 15 shows an example of such type. Many analytical implements packed in a cassette 69 are pushed out by a slider 70 one by one from the bottom and placed on the take-out position and ascertained by a detector 71. They are then picked up by the analytical implement holder 11 from this position.

E. Sample Vessel Supply Device, Optical Measurement Device

Though this embodiment uses a known sample vessel supply device 5 and optical measurement device 6, various modifications of them are available.

One example of the sample vessel supply device 5 is that of a turntable system. The turntable 72 is provided with many ports of receiving sample vessels 73 in the peripheral section and rotated in normal and reverse directions by a motor 75. If the turntable is made replaceable and successively changed, a great deal of samples can be treated.

The optical measurement device 6, on the other hand, comprises a light measuring section 76 and a reaction turntable 77 for leading the analytical implement 2 placed thereon. The reaction turntable 77 is provided radially thereon with a plurality of grooves 78 for putting an analytical implement 2 therein, and rotated intermittently in a direction by a motor 79. The light measuring section 76 is placed above a position where the groove 78 ends. The light measuring section 76 comprises an optical system 80 and a pulling device for moving the analytical implement 2. The motors 75 and 79 are preferably pulse motors.

F. Measuring Operation of Analysis Apparatus

The measuring operation by this automatic continuous analysis apparatus 1 is now described.

The arm 12 of the analytical implement automatic handling device 3 is moved outward (leftward in the drawing) by the rotation of the motor 20. At the same time, the rotary section 15 is brought down by the rotation of the motor 18 and the analytical implement holder 11 is brought to the analytical implement takeout position X of the analytical implement automatic supply device 4. Here, the open analytical implement holder 1 closes after catching the holding section of the analytical implement 2. Then, the motors 18 and 20 rotate in reverse direction, and the motor 14 for shaft rotation rotates to bring the analytical implement holder 11 to position Y for dipping the analytical implement in the dipping solution. The analytical implement holder 11 is lowered to dip the reagent section 2B in the sample solution for a specified time. Then, the motor 18 rotates to pull up the analytical implement 2, and the motors 10 and 14 rotate to bring the analytical implement holder 11 to the position Z of the turntable groove 78 on the optical measurement device. The analytical implement holder 11 puts the analytical implement 2 into the groove 78 by lowering from the upper side or by inserting it from the peripheral direction of the turntable.

The analytical implement 2 is sent to the light measuring section 76 by turning turntable 77, and measured. Then, the analytical implement holder 11 returns to position X and repeats the same action.

The action of these devices (3), (4), (5) and (6) is controlled by the microcomputer of the control section 7. It also calculates the concentration, etc., of each material to be examined from the reflectance, and displays the results on the display section 82. In FIG. 2, 83 indicates a printer, 84 an external output, and 85 a keyboard.

The liquid level detector is then described. In this invention, where the analytical implement 2 is automatically inserted into the sample vessel 73, if the sample solution is wanting in the vessel, the reagent section 2B fails to be dipped, of if it is too much, the dipping time becomes too long. Thus, accurate measurement is not to be expected.

To make the analysis more accurate, it is preferable to detect the level of the solution in advance and adjust the degree of insertion of the analytical implement 2 accordingly, or to issue a warning of the deficiency. The liquid level detection is effected, for example, by two long and short electrodes 87 and 88 supported on the end of the nozzle arm. The nozzle arm 86 is driven by a nozzle motor 89, and the electrodes 87 and 88 are washed in a washing tank 90 every measurement.

The long electrodes 87 can be used also as a suction nozzle to suck and lead the solution to a specific gravity unit 90 for specific gravity measurement.

However, since suction prior to analytical implement dipping can lower the liquid level, it is favorable to estimate the quantity or detect the liquid level in advance, and make dipping before suction.

These operations are effected by controlling the rotation of the turntable 72. The liquid level detection may be effected by an optical sensor using reflected light.

G. Effectiveness

As explained above, the method according to the invention holds up the analytical implement successively supplied by the supplier by gripping its holding section, and after dipping the reagent section on the analytical implement in the sample solution in the sample vessel (which is successively delivered), for a specified time, sets the analytical implement on the table, and after a specified time measures the light reflected by the reagent section.

Thus, all the operations such as dipping in the sample solution, optical measurement, calculation and disposal of the used sample solution can be carried out automatically using the Dip-and-Read type analytical implement. This largely lightens the load in the operator in comparison with the conventional method in which the "Dip" stage is performed manually, and largely reduces measuring error because variation of the time of dipping and time from the dipping to the start of measuring are greatly decreased. In addition, large labor saving is attained since the only work required by the operator is injection of the sample solution into the sample vessel. It can be used for general purpose because it can use general analytical implements for visual use without use of any special analytical implement for the automatic analysis apparatus.

The analytical implement supply device used in the invention stores analytical implements in the space enclosed by the bottom section having an analytical implement groove and two parallel walls which are parallel to the analytical implement groove, and takes out the analytical implements one by one fitted in the groove, by relatively reciprocating the bottom section to the walls.

Thus, the analytical implement can be taken out one by one with the reagent sections directed in one directly with certainty and this can be effected by putting them in the storage section with their holding sections arranged. In addition, normal analytical implements on the market can be used, and screening of different types and checking out of defectives are possible. This leads to increased reliability of the measurements. This invention, therefore, is simple in structure and operation.

What is claimed is:

1. An automatic continuous analysis method using an analytical implement having a reagent section, comprising: a transfer process and a measuring process, said transfer process including the steps of supplying analytical implements one by one from an automatic supply device, holding each analytical implement supplied by the automatic supply device by an analytical-implement automatic handling device, moving each analytical implement to a position above a sample vessel which is successively brought into a specified position where each analytical implement is to be dipped into the sample vessel, dipping each analytical implement in a sample solution in the sample vessel and pulling it up after a specified time, moving each implement above a reaction turntable and setting it on the reaction turntable and releasing each analytical implement from the analytical-implement automatic handling device, said measuring processing including the step of automatically measuring, after a specified time, light reflectance of the reagent section of each analytic implement.

2. The continuous automatic analysis method of claim 1, wherein said holding step is effected by holding each analytical implement by a gripping member of a driving arm associated with the analytical implement automatic handling devices.

3. An automatic continuous analysis method using an analytical implement with a reagent section as claimed in claim 1, including the steps of measuring the liquid level of the sample solution in the sample vessel prior to dipping the reagent section of each analytical implement and determining the depth of dipping each analytical instrument according to the liquid level.

4. In the continuous automated analysis method of claim 1, an automatic method of taking out analytical implements for said supplying step including the steps of putting many analytical implements in a storage section comprising a bottom section provided with an analytical implement groove and an inside wall surface which is parallel with the groove, moving said groove in normal and reverse directions relative to the wall surface while checking for the presence of an analytical implement in the groove by a detector on the wall surface, and stopping said movement at a specified position after ascertaining that an analytical implement has been fitted in the groove.

5. The continuous automated analysis method of claim 4 wherein the automatic method of taking out analytical implements includes, by utilizing an inversion device, the steps of pushing out an analytical implement which has been fitted into the groove in a reversed bottom-top direction, inverting the analytical implement toward the wall and refitting it into the groove while the bottom section goes back in reverse direction.

6. The continuous automated analysis method of claim 4 wherein the automatic method of taking out analytical implements includes, the steps of removing it, by a removing device in the stop position or vicinity, by pushing it out toward the direction opposite to the wall.

7. The continuous automated analysis method of claim 4, wherein the automatic method of taking out analytical implements, includes, when an analytical implement fitted into the groove is a non-conforming one, removing it from the groove and returning it into the hopper and taking out another analytical implement to be caught by the groove.

8. An automatic continuous analysis apparatus for use with an analytical implement having a reagent section, said apparatus comprising an automatic handling section, a control section and a keyboard and display section, said automatic handling section including:

an analytical-implement automatic handling device;
an analytical-implement automatic supply device provided with a hopper into which analytical implements to be put, a sample-vessel supply device, and an optical measurement device being arranged around said analytical-implement automatic handling device:

said hopper including a bottom section provided with a groove for accommodating an analytical implement and wall sections, one of which is parallel with the groove viewed in a plane at least at a lower edge of the inside surface of the wall; and said bottom section being separated from said wall section and wherein at least a part of the bottom section can advance and return relative to the wall section so that at least said groove can reach positions both inside and outside of the wall section;

said control section controlling the rotation of motors for making the analytical-implement holder move to an analytical-implement take-out position of the analytical-implement automatic supply device and to a position for putting each analytical implement into the turntable groove on the optical measurement device, successively; the control section also controlling the action of the analytical-implement automatic handling device, the sample-vessel supply device, and the turntable and the light measuring section on the optical measurement device; and said keyboard and said display section exchanging signals with the control section.

9. An automatic continuous analysis apparatus using an analytic implement as claimed in claim 8, including a detector, which is provided on or near the wall section on the side where the analytical implement groove passes, for detecting an analytical implement caught by the groove.

10. An automatic continuous analysis apparatus using an analytical implement having a reagent section comprising:
an analytical implement automatic supply device;
a sample vessel supplying device;
an analytical implement handling device which is provided with an analytical implement holder on an end of an arm capable of being driven right-and-left, up-and-down, and rotatingly;
a light measuring device including a reaction turntable for providing measured data;
means for controlling the operation of said apparatus by directing the analytical implement holder to successively move to a take-out position of the analytical implement automatic supply device, an analytical implement dipping position of the sample vessel supply device and an analytical implement mounting position of the light measuring device and for controlling the drive of the analytical implement automatic handling device, the sample vessel supplying device, the reaction table of the light measuring device and the light measuring device; and
a display section cooperating with said control means for displaying measured data.

11. An automatic continuous analysis apparatus having an analytical implement automatic supplying device as claimed in claim 10, including an analytical implement hopper having a bottom section with an analytical implement groove, wherein at least one wall surfaces other than one which is parallel with the analytical implement groove and one opposite to it is parallel with a moving direction of the analytical implement groove, and the bottom surface is inclined so that it is lower at one the parallel inside wall surfaces than the other.

12. An automatic continuous analysis device as claimed in claim 11 which is provided on the outside of the wall where the analytical implement groove passes, with an inversion device for inverting an analytical implement fitted in the analytical implement groove reversely in top-and-bottom direction.

13. An automatic continuous analysis device as claimed in claim 11 which is provided on the outside of the wall where the analytical implement groove passes, with a removing device for removing a non-conforming analytical implement by pressing it in opposite direction to the wall.

* * * * *